United States Patent
Umebayashi et al.

(10) Patent No.: US 12,202,212 B2
(45) Date of Patent: Jan. 21, 2025

(54) METHOD FOR MANUFACTURING WEARABLE ARTICLE

(71) Applicant: ZUIKO CORPORATION, Osaka (JP)

(72) Inventors: Toyoshi Umebayashi, Osaka (JP); Natsuki Ikeda, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 162 days.

(21) Appl. No.: 17/921,744

(22) PCT Filed: May 7, 2021

(86) PCT No.: PCT/JP2021/017570
§ 371 (c)(1),
(2) Date: Oct. 27, 2022

(87) PCT Pub. No.: WO2021/225169
PCT Pub. Date: Nov. 11, 2021

(65) Prior Publication Data
US 2023/0166459 A1 Jun. 1, 2023

(30) Foreign Application Priority Data
May 8, 2020 (JP) .................................. 2020-082674

(51) Int. Cl.
*B29C 65/00* (2006.01)
*B29C 65/18* (2006.01)
(Continued)

(52) U.S. Cl.
CPC .............. *B29C 66/21* (2013.01); *B29C 65/18* (2013.01); *B29C 65/7894* (2013.01); *B29L 2031/4878* (2013.01)

(58) Field of Classification Search
None
See application file for complete search history.

(56) References Cited

U.S. PATENT DOCUMENTS 10,561,540 B2   2/2020  Mori et al.
2015/0328055 A1  11/2015  Shimada
(Continued)

FOREIGN PATENT DOCUMENTS

CN   105682628    6/2016
JP   2013-199090  10/2013
(Continued)

OTHER PUBLICATIONS

Machine English translation of JP2016112340 (Year: 2016).*
(Continued)

*Primary Examiner* — Jacob T Minskey
*Assistant Examiner* — Adrianna N Konves
(74) *Attorney, Agent, or Firm* — Wenderoth, Lind & Ponack, L.L.P.

(57) ABSTRACT

A method for manufacturing a wearable article includes: superposing first and second parts of a continuous material on each other; winding the continuous material around a rotary drum and conveying the continuous material; moving a movable part of a sealer unit outward and homeward in a cross direction crossing a conveyance direction, while the continuous material is conveyed, to form linear sealing areas and joining the first part and the second part through the formed linear sealing areas; and after the superposing and before the joining, inhibiting a movement of the first part and the second part relative to each other by temporary fastening at a place at which the first part and the second part are to be joined together.

21 Claims, 16 Drawing Sheets

(51) Int. Cl.
*B29C 65/78* (2006.01)
*B29L 31/48* (2006.01)

(56) References Cited

U.S. PATENT DOCUMENTS

2016/0250082 A1  9/2016  Hamamoto et al.
2017/0007466 A1  1/2017  Yamamoto et al.

FOREIGN PATENT DOCUMENTS

| JP | 2016-112237 | 6/2016 |
| JP | 2016-112340 | 6/2016 |
| JP | 2018-61545 | 4/2018 |
| WO | 2014/097636 | 6/2014 |
| WO | 2015/098535 | 7/2015 |
| WO | 2015/129297 | 9/2015 |

OTHER PUBLICATIONS

Machine English translation of WO2015098535 (Year: 2015).*
Office Action issued Feb. 18, 2023 in corresponding Chinese Patent Application No. 2021800319231, with English language translation.
International Search Report issued Jul. 20, 2021 in International (PCT) Application No. PCT/JP2021/017570.
Extended European Search Report issued Aug. 11, 2023 in corresponding European Patent Application No. 21800966.0.

* cited by examiner

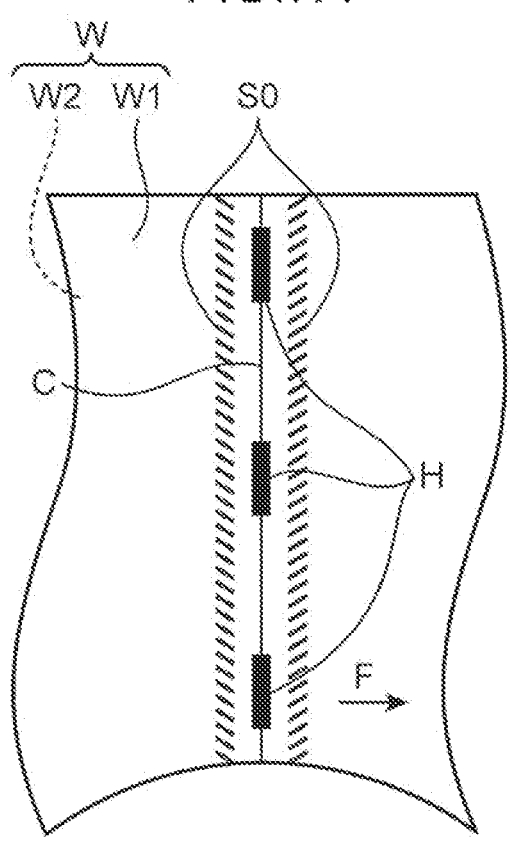

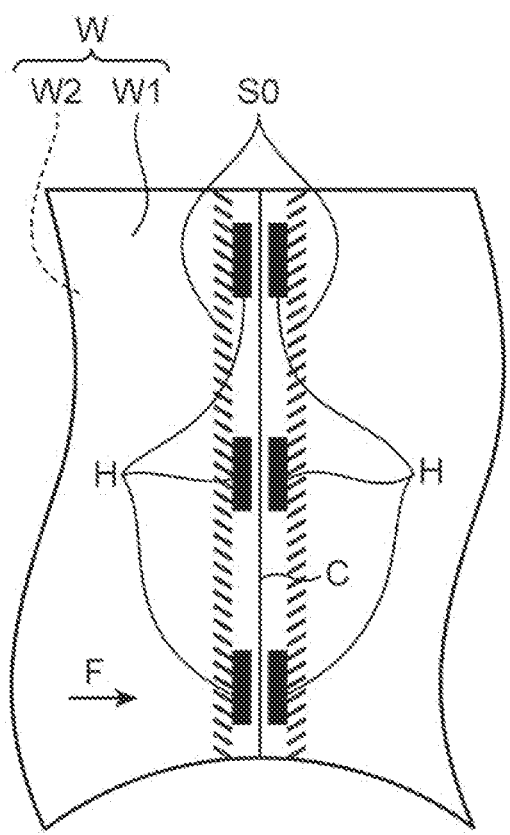

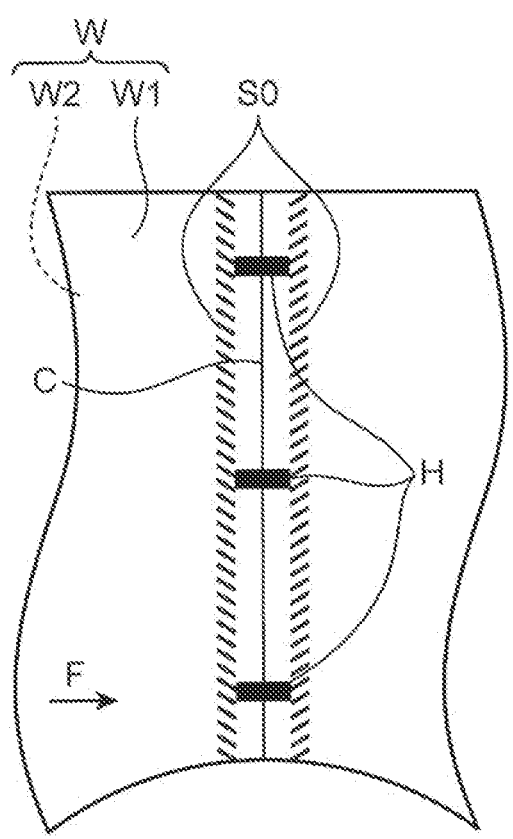

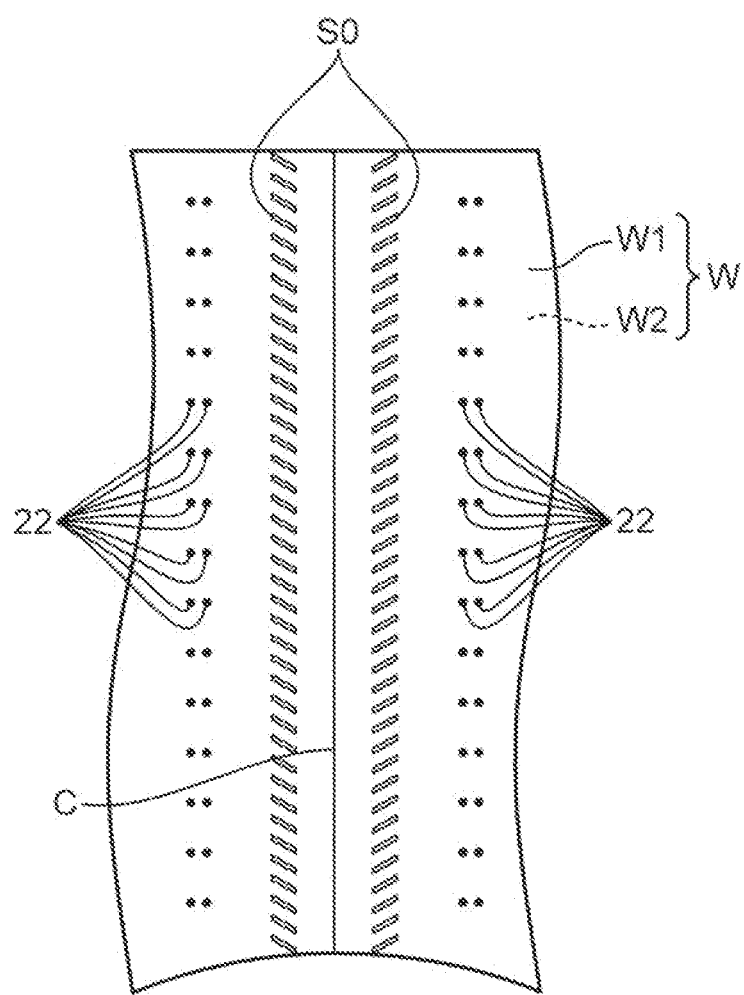

METHOD FOR MANUFACTURING WEARABLE ARTICLE

TECHNICAL FIELD

The present invention relates to a method for manufacturing a wearable article.

BACKGROUND ART

Conventionally, there have been various methods proposed for manufacturing wearable articles such as disposable diapers continuously.

For instance, a method for manufacturing a wearable article, described in WO 2015/098535 A, involves superposing a front body part and a back body part of a continuous material on each other, the front body part and the back body part making up a wearable article, and winding the continuous material including the front body part and the back body part superposed on each other around a rotary drum to convey the continuous material. The method also involves moving an anvil roller of a sealer unit outward and homeward along straight travel paths in a direction crossing a direction in which the continuous material is conveyed, with the sealer unit being rotated at a rate identical to that of the rotary drum, while the continuous material including the superposed front body part and back body part is conveyed by the rotary drum, and thereby joining the front body part and the back body part to each other through linear sealing areas along the outward-and-homeward travel paths in an area of either end of each wearable article in the continuous material.

However, the method for manufacturing a wearable article, shown in WO 2015/098535 A, causes a difference in peripheral velocity between one of the front body part and the back body part disposed on an inner periphery side of the drum and the other body part disposed on an outer periphery side (for example, see a first part W1 and a second part W2 of a continuous material W in FIG. 11) when the continuous material, from which wearable articles are made, is wound around the rotary drum with the front body part and the back body part being superposed on each other.

As a result, there is a problem of the occurrence of a discrepancy in sealing area between the outward and homeward paths due to the occurrence of a peripheral velocity difference between the sealer unit and either the front body or the back body (for example, see sealing areas S1, S2 in FIG. 12) when the parts of the continuous material are joined to each other by an outward-and-homeward movement of the sealer unit in the direction crossing the direction in which the continuous material is conveyed.

Such a discrepancy (or misalignment) in sealing area has a dimension of 1 mm or more that is visible on a peripheral surface of an ordinarily used rotary drum with a large diameter of approximately 2 m, and the discrepancy is further noticeable especially for a wearable article such as an underpants-type diaper that includes a thick absorber.

SUMMARY OF INVENTION

It is an object of the present invention to provide a method for manufacturing a wearable article with a capability to reduce a discrepancy between sealing areas on outward and homeward paths through which superposed parts of a continuous material are joined to each other.

A method of the present invention for manufacturing a wearable article, accomplished to solve the above challenge, includes: a superposing step of superposing a first part and a second part of a wearable article on each other, the wearable article being included in a continuous material; a conveying step of winding the continuous material including the first part and the second part superposed on each other around an outer peripheral surface of a rotary drum and conveying the continuous material by rotation of the rotary drum; and a joining step of moving a movable part of a sealer unit outward and homeward in a cross direction crossing a conveyance direction in which the continuous material is conveyed, with the sealer unit being rotated at a rate identical to a rate of the rotary drum while the continuous material is conveyed by the rotation of the rotary drum, to form linear sealing areas on an outward path and a homeward path, respectively, and thereby joining the first part and the second part to each other through the formed linear sealing areas in areas corresponding to both sides of the wearable article, the method further comprising, after the superposing step and before the joining step, a discrepancy reduction step of inhibiting a movement of the first part and the second part relative to each other at a place at which the first part and the second part are to be joined together.

BRIEF DESCRIPTION OF DRAWINGS

FIG. 7A is an illustrative drawing showing a thermal fusion pattern, i.e., an arrangement of heat sealing areas, formed on the continuous material by the thermally fusing unit of FIG. 5.

FIG. 7B is an illustrative drawing showing another thermal fusion pattern, i.e., another arrangement of heat sealing areas, formed on the continuous material by the thermally fusing unit of FIG. 5.

FIG. 7C is an illustrative drawing showing another thermal fusion pattern, i.e., another arrangement of heat sealing areas, formed on the continuous material by the thermally fusing unit of FIG. 5.

FIG. 10A is an enlarged elevation view of the continuous material penetrated by the needles in FIG. 9.

DESCRIPTION OF EMBODIMENTS

Hereinafter, a preferred embodiment of the present invention will be described in detail with reference to the attached drawings.

Figure 1:
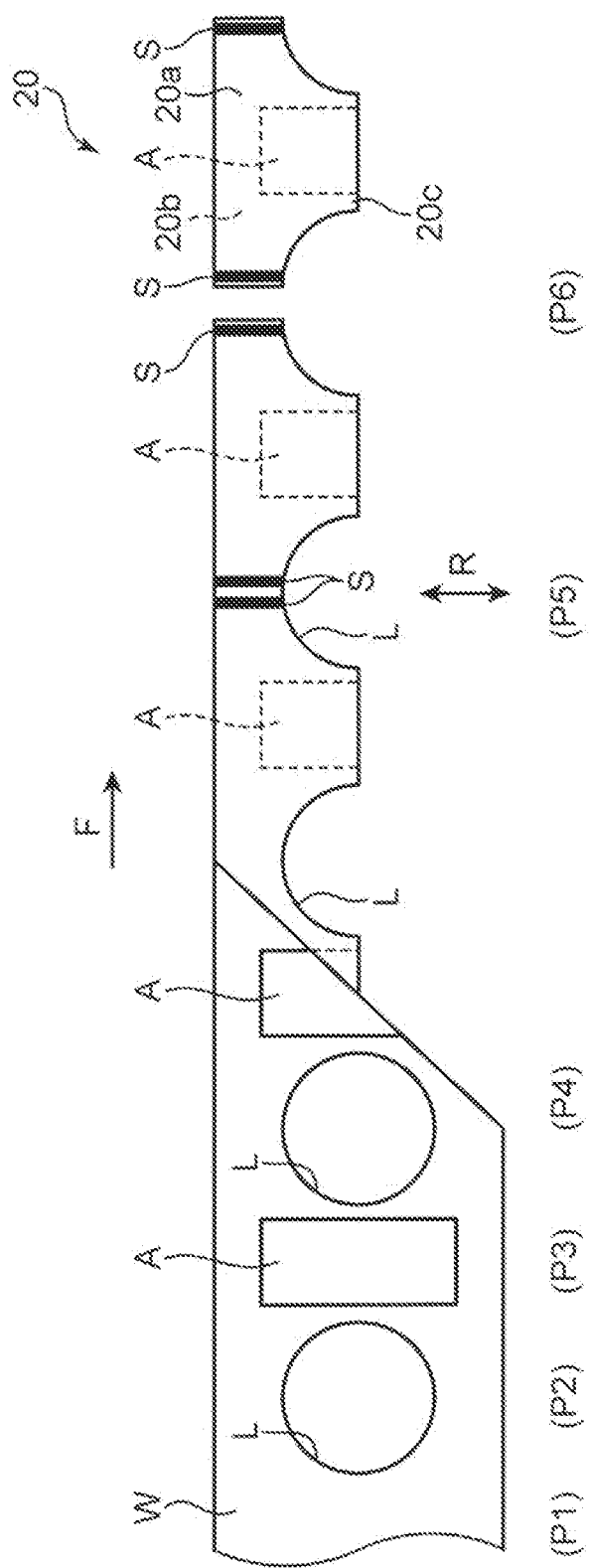
FIG. 1 is a process drawing for illustrating a method for manufacturing a disposable diaper as an example of a method for manufacturing a wearable article according to a first embodiment of the present invention.

A wearable article 20 manufactured by a manufacturing method of the present invention is, for example, a wearable article such as a disposable diaper or underpants that can cover a lower half of one's body, as shown in FIG. 1, and includes a front body 20a disposed on an abdomen of a wearer wearing the wearable article, a back body 20b disposed on buttocks of the wearer, and a crotch 20c extending from the front body 20a to the back body 20b through an area between the tops of the wearer's legs.

Both side edges of the front body 20a and both side edges of the back body 20b are joined together such that the coupled front body 20a and back body 20b form an annular shape. Specifically, the front and the back bodies are welded to each other through two sealing areas S by ultrasonic welding.

A basic procedure for manufacturing the wearable article 20 is as described below.

<Conveying Step P1>

In a conveying step P1, a long sheet-shaped continuous material W extending in a specific direction is conveyed along a lengthwise direction of the material (a conveyance direction F). A description is given hereinafter with a direction in which the continuous material W is carried being defined as a lateral direction and a direction orthogonal to the lateral direction in FIG. 1 as a longitudinal direction.

The continuous material W includes an inside sheet facing a body surface of the wearer wearing the wearable article, an outside sheet facing outward from the wearer wearing the wearable article, and an elastic member that is put between the inside sheet and the outside sheet and that is elastic at least in the conveyance direction F. The outside sheet is made of a nonwoven sheet and/or a mesh sheet which are permeable to liquid, or a polyethylene film, a polypropylene film, or a heat seal resin-made nonwoven fabric that is waterproof and breathable.

<Leg Hole Forming Step P2>

In a leg hole forming step P2, a leg hole L is formed at a middle in the longitudinal direction of the continuous material W.

A region between the two leg holes L in the continuous material W is a part corresponding to the crotch 20c. Places on both sides of the part corresponding to the crotch 20c in the longitudinal direction of the continuous material W are parts corresponding to the front body 20a and the back body 20b, respectively.

In other words, the conveying step P1 and the leg hole forming step P2 correspond to a preparation step for preparing a continuous material in which constituent elements are consecutive in the lateral direction. Each of the constituent elements is formed by the front body 20a and the back body 20b being coupled through the crotch 20c in the longitudinal direction.

<Absorber Joining Step P3>

In an absorber joining step P3, an absorptive body A is joined to a place between the two leg holes L in the continuous material W.

The absorptive body A includes a permeable sheet permeable to liquid, a waterproof sheet that is waterproof and breathable, and an absorptive core put between the permeable sheet and the waterproof sheet. The permeable sheet is made of a nonwoven sheet and/or a mesh sheet which are permeable to liquid. The waterproof sheet is made of a polyethylene film, a polypropylene film, or a nonwoven fabric that is waterproof and breathable. The absorptive core is shaped by laminating crushed pulp or crushed pulp mixed with a super absorbent polymer.

<Superposing Step P4>

In a superposing step P4, the continuous material W on which the absorptive body A is placed is folded in half in the longitudinal direction (in other words, at a middle position in a widthwise direction (the longitudinal direction) of the continuous material W). As a result, the part corresponding to the front body 20a and the part corresponding to the back body 20b of the continuous material W are superposed on each other.

<Joining Step P5>

In a joining step P5, a part corresponding to a side edge of the front body 20a and a part corresponding to a side edge of the back body 20b of the continuous material W folded in half are joined together by ultrasonic welding.

Specifically, in the joining step P5, the parts at two places of the continuous material W are separated from each other via a cutting zone that is set in advance as a zone to be cut in a cutting step P6 described later. The parts at two places are simultaneously joined together by ultrasonic welding to form linear sealing areas S extending in a cross direction R that crosses (that is orthogonal to, in the present embodiment) the conveyance direction F.

The two sealing areas S are formed on the parts corresponding to the side edges of the front body 20a and on the parts corresponding to the side edges of the back body 20b.

<Cutting Step P6>

In the cutting step P6, the continuous material W is cut along a cutting line extending longitudinally between the two sealing areas S formed in the joining step P5. As a result, the continuous material W is cut on a wearable article by wearable article basis.

<Description of Ultrasonic Welding Device 1>

Figure 6:
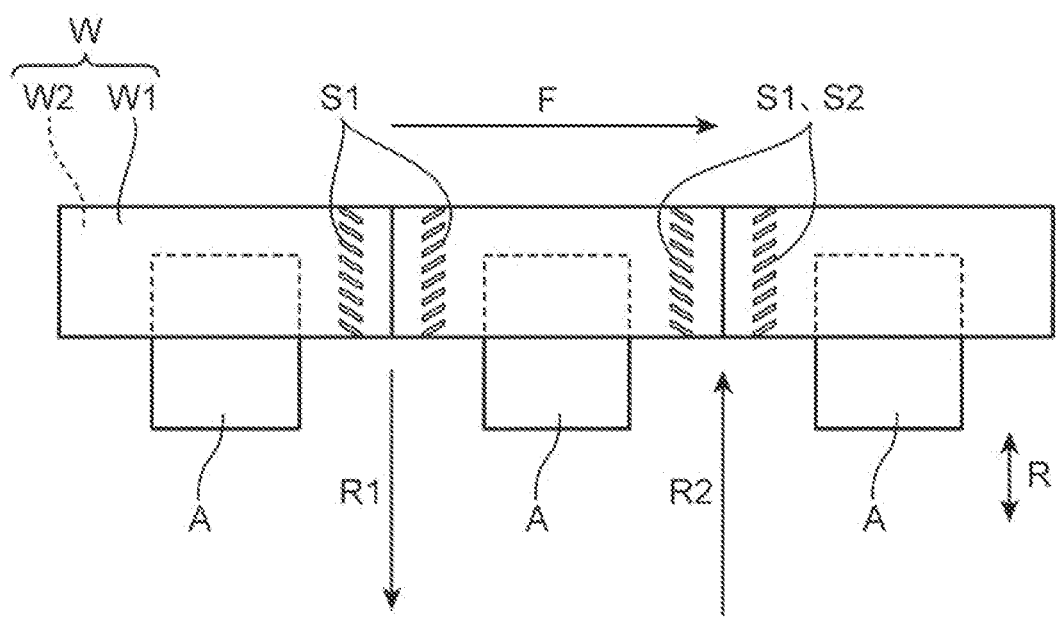
FIG. 6 is an illustrative drawing showing a joining step executed by the ultrasonic welding device of FIG. 2 to form outward and homeward sealing areas.

A joining device used to execute the joining step P5 is configured to move a movable part of a sealer unit outward and homeward in a cross direction R crossing a conveyance direction F in which the continuous material W is conveyed, while the continuous material W is conveyed by the rotation of the rotary drum 5, to form linear sealing areas S1, S2 shown in FIG. 6 on an outward path R1 and a homeward path R2, respectively, and thereby join the first part W1 and the second part W2 to each other through the formed linear sealing areas in areas corresponding to both sides of the wearable article 20. For instance, an ultrasonic welding device 1 shown in FIG. 2 is used to execute the joining step P5.

Figure 2:
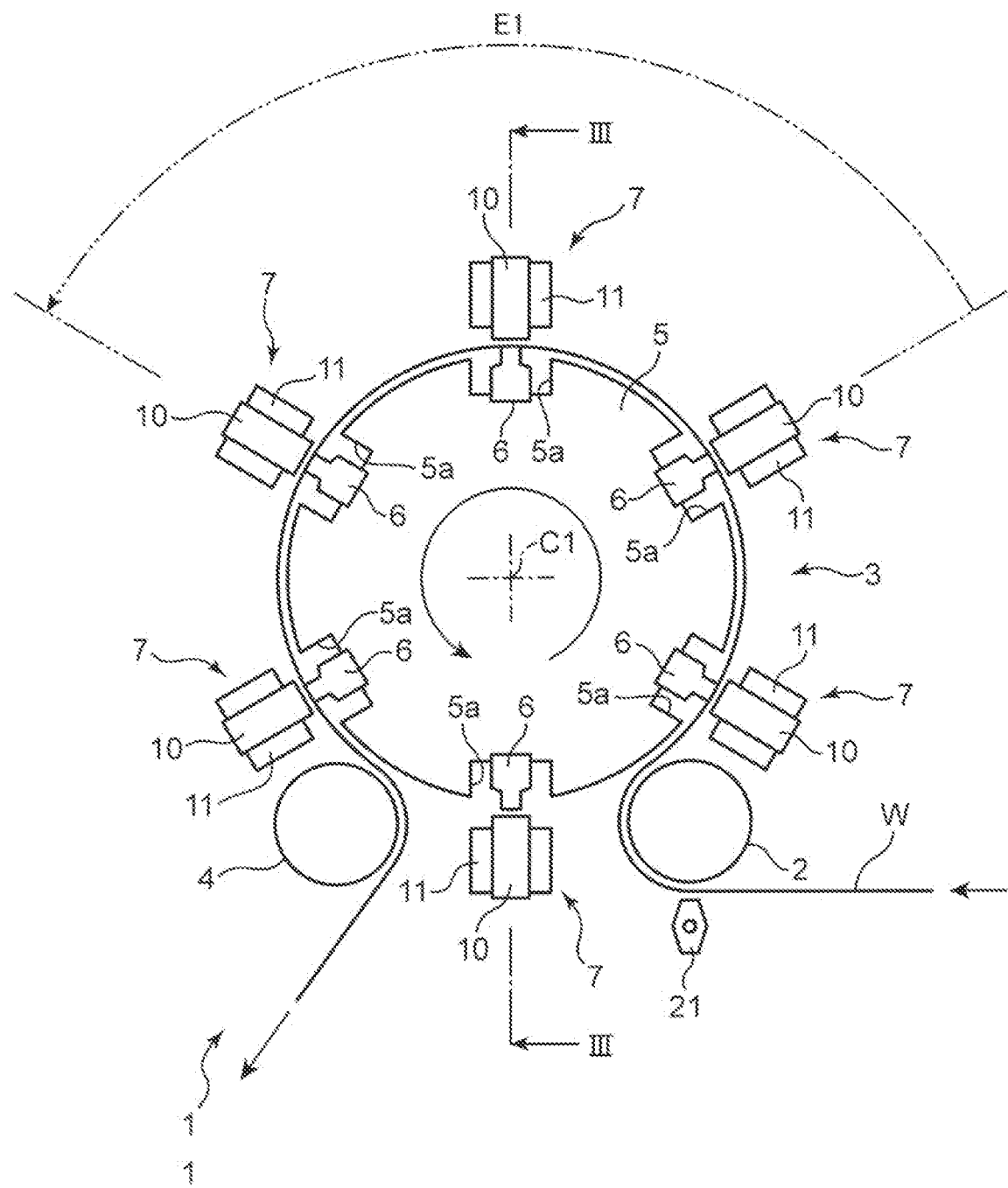
FIG. 2 is a schematic elevation view showing a configuration of an ultrasonic welding device used to execute a joining step shown in FIG. 1.

The ultrasonic welding device 1 shown in FIG. 2 includes a bring-in anvil roller 2 to bring in the continuous material W folded in half in the superposing step P4, a welding drum unit 3 to weld the continuous material W brought in by the bring-in anvil roller 2, and a bring-out anvil roller 4 to bring out the continuous material W welded by the welding drum unit 3.

The welding drum unit 3 includes a rotary drum 5 to hold the continuous material W brought in by the bring-in anvil roller 2 and six ultrasonic sealer units 7 serving as a sealer unit for joining of the continuous material W to ultrasonically weld the continuous material W.

Figure 3:
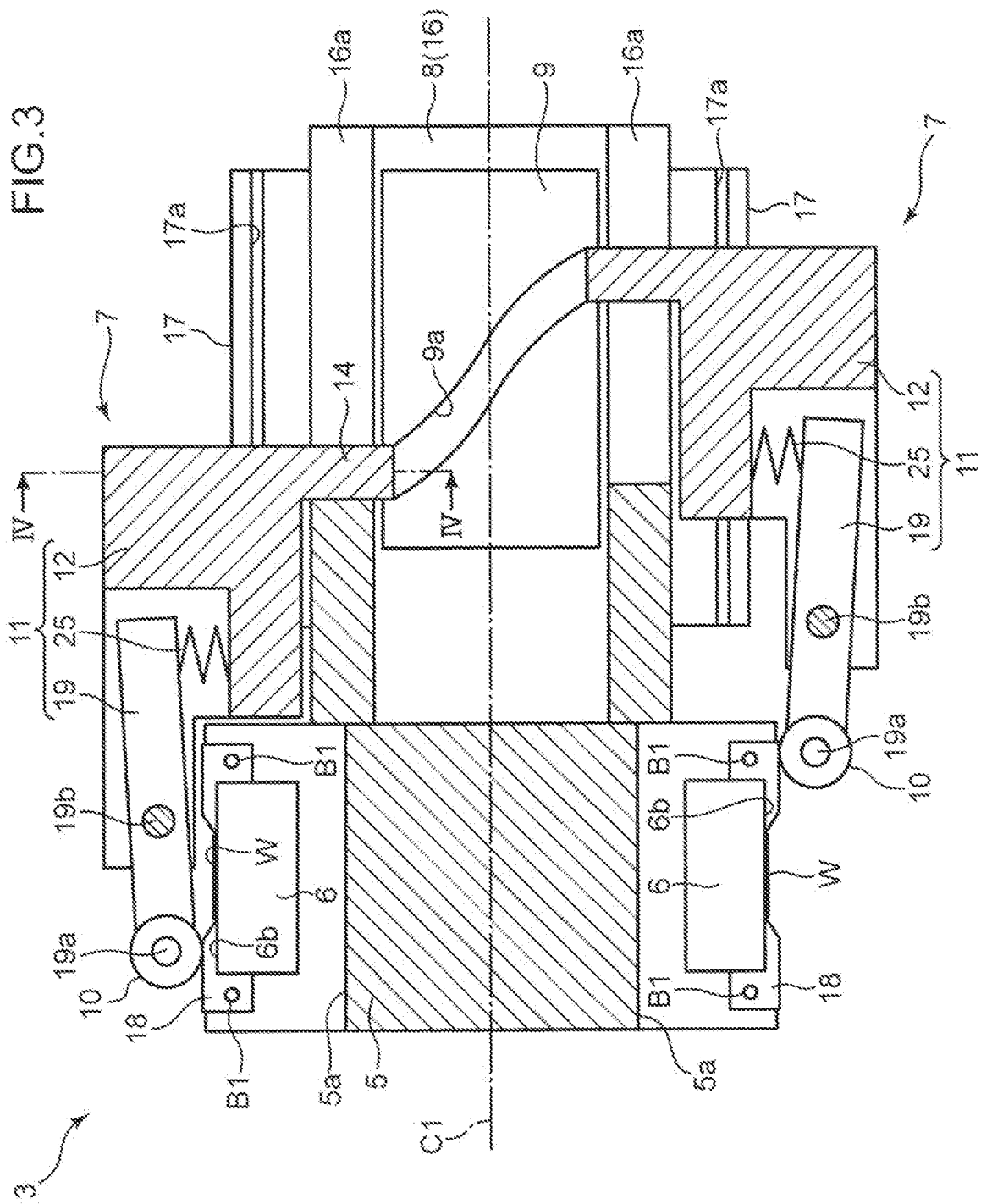
FIG. 3 is a cross-sectional view taken along line III-III of FIG. 2.

The ultrasonic sealer units 7, as shown in FIGS. 2 to 3, include six ultrasonic horns 6 disposed on the rotary drum 5, anvil rollers 10 (movable parts) to weld the continuous material W in conjunction with the ultrasonic horns 6, and holding members 11 to hold the respective anvil rollers 10 in such a way as to be movable relative to the rotary drum 5 along a rotation center C1 (i.e., movable in a superior-inferior direction in FIG. 3).

The welding drum unit 3 also includes an anvil holding drum 8 (see FIG. 3) in a shape of a tube to hold the holding members 11, a cam drum 9 (see FIG. 3) disposed inside the anvil holding drum 8, and six pressed members 18 (see FIG. 3) that are adjacent to the respective ultrasonic horns 6 and fixed to the rotary drum 5.

As shown in FIGS. 2 to 3, the rotary drum 5 is able to rotate on the rotation center C1 with the continuous material W being held on an outer peripheral surface of the rotary drum. Six recessed grooves 5a are formed around the rotation center C1 at equal intervals on the rotary drum 5. The recessed grooves 5a are opened outward from the rotary drum 5, extending along the rotation center C1.

The ultrasonic horns 6 apply ultrasonic vibration to the continuous material W held by the rotary drum 5. Each ultrasonic horns 6 have an output side end 6b to output the ultrasonic vibration.

The ultrasonic horn 6, as shown in FIGS. 2 to 3, is disposed in the recessed groove 5a so as to come into contact with the continuous material W held by the rotary drum 5 from inside.

Figure 4:
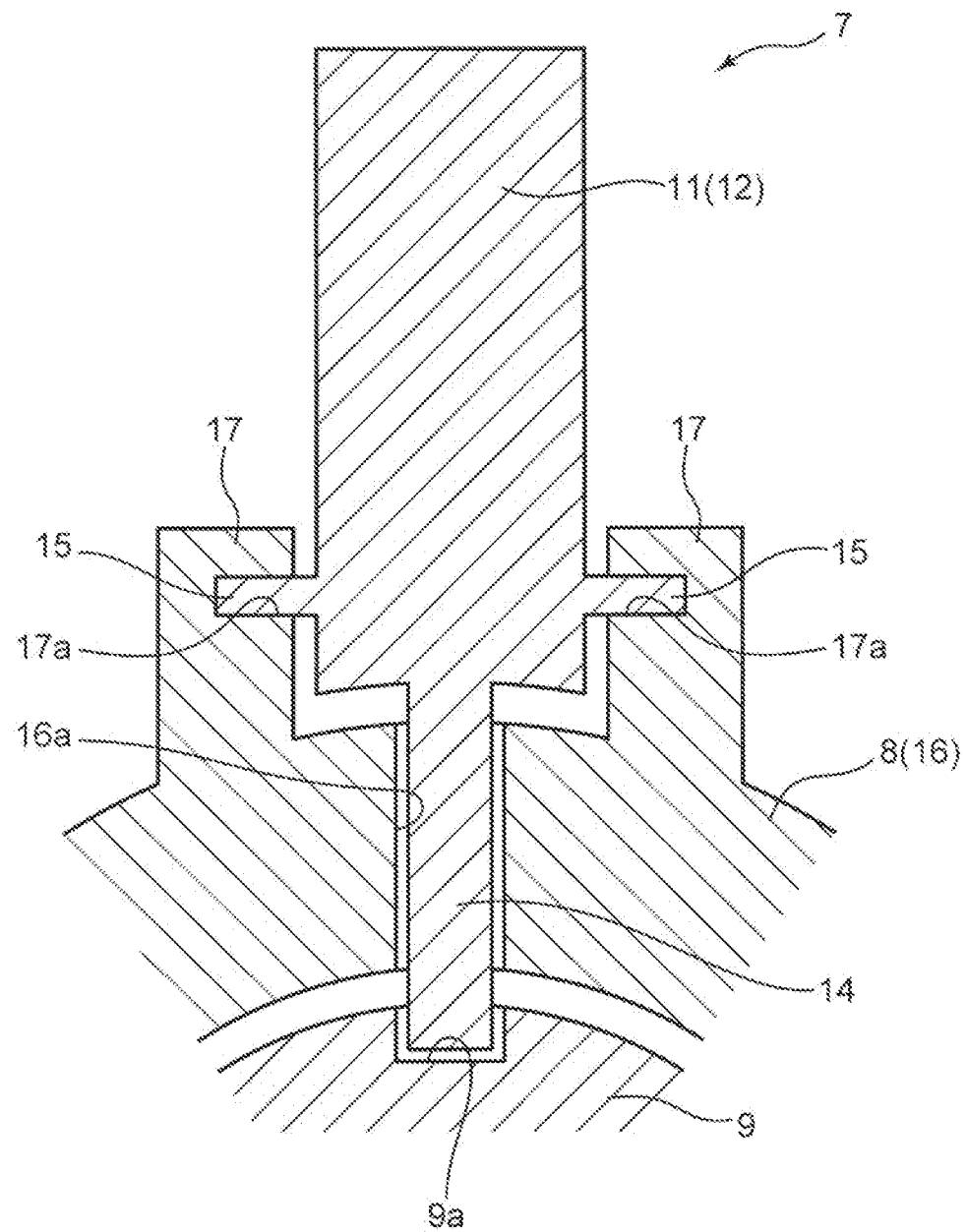
FIG. 4 is a cross-sectional view taken along line IV-IV of FIG. 3.

As shown in FIGS. 3 to 4, the holding member 11 includes a holding member body 12 attached to the anvil holding drum 8 so as to be movable along the rotation center C1, a holding lever 19 that is attached to the holding member body 12 so as to be pivotable around a pivot 19b and that holds the anvil roller 10 such that the anvil roller is rotatable on a rotation axis 19a, and a push member 25 that pushes the holding lever 19 in such a direction that the anvil roller 10 moves toward the ultrasonic horn 6.

The rotation axis 19a and the pivot 19b are axes each extending in a direction orthogonal to a plane including the rotation center C1 and the ultrasonic sealer units 7 (a direction orthogonal to a piece of paper of FIG. 3). The rotation axis 19a is disposed on a distal end of the holding lever 19, whereas the pivot 19b is disposed on a middle of the holding lever 19.

Thus, the anvil roller 10 is able to come into contact with and roll over the continuous material W in response to a movement of the holding member 11 along the rotation center C1 and is able to move toward or away from the continuous material W (the ultrasonic horn 6) in a radial direction of the rotary drum 5 in response to a pivot of the holding lever 19.

The push member 25 pushes a proximal end of the holding lever 19 with respect to the holding member body 12 in a direction in which the proximal end moves away from the rotation center C1 and thereby pushes the anvil roller 10 in a direction in which the anvil roller 10 moves toward the ultrasonic horn 6.

The push member 25, the holding lever 19, and the pivot 19b correspond to a push mechanism designed to push the anvil roller 10 toward the ultrasonic horn 6 such that the ultrasonic horn 6 and the anvil roller 10 move toward each other.

The holding member body 12 has a cam protrusion 14 extending toward the rotation center C1 and a pair of engagement protrusions 15 protruding in opposite directions along a direction (a crosswise direction in FIG. 4) orthogonal to both the cam protrusion 14 and the rotation center C1 and extending along the rotation center C1.

The holding member body 12 is disposed between a pair of rails 17 that stand on an outer peripheral surface of the anvil holding drum 8. The rails 17 each have an engagement groove 17a being opened to the opposite rail 17 side and extending along the rotation center C1. The engagement protrusions 15 of the holding member body 12 are in engagement with the respective engagement grooves 17a such that the engagement protrusions 15 are movable relative to the anvil holding drum 8 along the rotation center C1.

The tubular anvil holding drum 8 includes a slit 16a penetrating through a peripheral wall of the anvil holding drum and extending along the rotation center C1. The cam protrusion 14 of the holding member body 12 is inserted into the anvil holding drum 8 through the slit 16a.

The cam drum 9 is disposed inside the anvil holding drum 8, and a cam groove 9a is formed on an outer peripheral surface of the cam drum 9. A distal end of the cam protrusion 14 is inserted into the cam groove 9a. The cam groove 9a guides the cam protrusion 14 such that each ultrasonic sealer unit 7 moves along the rotation center C1 in response to rotation of the anvil holding drum 8 relative to the cam drum 9.

The rotary drum 5 and the anvil holding drum 8 are fastened to each other and rotate on the rotation center C1 in an integral manner. Meanwhile, a rotational position of the cam drum 9 is fixed regardless of the rotation of the rotary drum 5 and the anvil holding drum 8. Thus, the holding member body 12 moves along the rotation center C1 in response to the rotation of the rotary drum 5 and the anvil holding drum 8 on the rotation center C1.

Specifically, the anvil roller 10 and the holding member 11 at a lowest place in FIGS. 2 and 3 is disposed at a place separated from the continuous material W held by the rotary drum 5 in plan view. The anvil roller 10 and the holding member 11 in this state move toward the continuous material W along the rotation center C1 in response to counterclockwise rotation of the rotary drum 5 in FIG. 2.

In a course of displacement of the anvil roller 10 and the holding member 11 to a highest place in FIGS. 2 and 3, the anvil roller 10 crosses the continuous material W, and the anvil roller 10 at the highest place in FIGS. 2 and 3 is disposed at a place separated from the continuous material W held by the rotary drum 5 in plan view. The anvil roller 10 in this state crosses the continuous material W again in response to further counterclockwise rotation of the rotary drum 5 and returns to a position of the anvil roller 10 at the lowest place in FIGS. 2 and 3.

In other words, in a range E1 in FIG. 2, the anvil roller 10 of the ultrasonic welding device 1 moves outward and homeward on the continuous material W, and during this outward-and-homeward movement, the continuous material W is welded at parts of the sealing areas S. More specifically, the anvil rollers 10 positioned in a range outside the range E1 in FIG. 2 are at places separated from the continuous material W in plan view. When the anvil rollers 10 come in the range E1, the anvil rollers 10 move successively to a place that overlaps the continuous material W in plan view.

First Embodiment

A method of a first embodiment for manufacturing the wearable article 20 is implemented through the following procedure using the ultrasonic welding device 1 described above.

Figure 5:
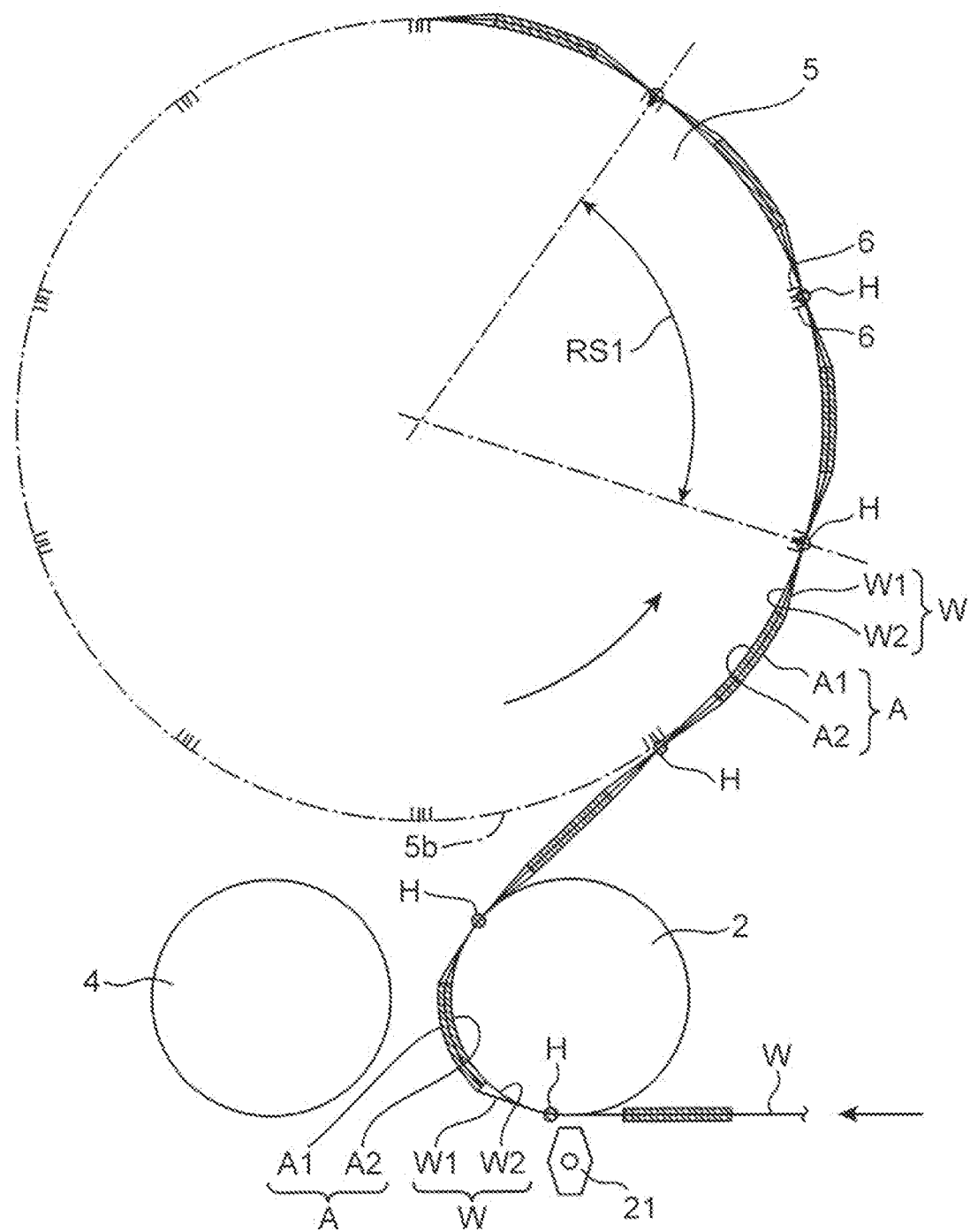
FIG. 5 is an illustrative drawing showing a process as an example of a discrepancy reduction step executed to thermally fuse a first part and a second part of a continuous material on an upstream side of a rotary drum in FIG. 2, with the first part and the second part being superposed on each other.

Specifically, the method of the first embodiment for manufacturing a wearable article 20 includes:
(i) a superposing step (see the superposing step P4 in FIG. 1) of superposing a first part W1 and a second part W2 of a wearable article 20 on each other, the wearable article 20 being included in a continuous material W, the first part W1 and the second part W2 corresponding to a front body and a back body respectively of the wearable article 20;
(ii) a conveying step (in other words, a conveying step between the superposing step P4 and the joining step P5 in FIG. 1) of winding the continuous material W including the first part W1 and the second part W2 superposed on each other around an outer peripheral surface 5b of a rotary drum 5, as shown in FIG. 5, and conveying the continuous material W by rotation of the rotary drum 5; and
(iii) a joining step (the joining step P5 in FIG. 1) of moving an anvil roller 10 that is a movable part of each ultrasonic sealer unit 7 in FIGS. 2 to 3 outward and homeward in a cross direction R crossing a conveyance direction F in which the continuous material W is conveyed, with each of the ultrasonic sealer units 7 being rotated at a rate identical to a rate of the rotary drum 5 (for example, while the rotary drum 5 in FIG. 5 is rotated in a predetermined angular range RS1), while the continuous material W is conveyed by the rotation of the rotary drum 5, to form linear sealing areas S1, S2 shown in FIG. 6 on an outward path R1 and a homeward path R2, respectively, and thereby joining the first part W1 and the second part W2 to each other (ultrasonic welding in the present embodiment) through the formed linear sealing areas in areas corresponding to both sides of the wearable article 20.

The manufacturing method of the first embodiment includes, after the superposing step and before the joining step, (iv) a discrepancy reduction step of inhibiting a movement of the first part W1 and the second part W2 relative to each other at a place at which the first part W1 and the second part W2 are to be joined together.

In the discrepancy reduction step of the first embodiment, the first part W1 and the second part W2 are temporarily fastened to each other at a scheduled joining place S0 (see FIGS. 7A, 7B, and 7C) at which the first part W1 and the second part W2 are scheduled to be joined together or in an area adjacent to the scheduled joining place.

The temporary fastening is implemented, for example, by thermal fusion (in other words, heat sealing). Specifically, at a peripheral surface of the bring-in anvil roller 2 on an upstream side of the rotary drum 5 shown in FIGS. 2 and 5, the superposed first part W1 and second part W2 of the continuous material W are heat-sealed using a heat sealer unit 21.

As shown with heat sealing areas H in FIGS. 7A, 7B, and 7C, heat sealing, for example, forms a vertically- or horizontally-oriented pattern of heat sealing areas at places associated with a waist part (an upper end of the first part W1), a tummy part (a middle of the first part W1), and a leg part (a lower end of the first part W1) of the wearable article 20 (see FIG. 1). Preferably, heat sealing is performed, as shown in FIGS. 7A, 7B, and 7C, on a scheduled cut place C at which each wearable article 20 is cut off rather than on the scheduled joining place S0 to avoid detachment and other influence on an ultrasonically welded seal applied to the scheduled joining place S0 in the joining step.

In other words, as shown in FIGS. 7A, 7B, and 7C, heat sealing is performed on a plurality of points in a region between two scheduled joining places S0 such that a plurality of heat sealing areas H are simultaneously formed at intervals equally separated from each other in a full width of the first part W1 and the second part W2.

For instance, as shown in FIG. 7A, heat sealing areas H are formed at a plurality of places separated from each other along the scheduled cut place C between adjacent wearable articles 20 included in the continuous material W.

As shown with heat sealing areas H in FIG. 7B, heat sealing may be performed on places on both sides of the scheduled cut place C between the adjacent wearable articles 20 included in the continuous material W.

Further, as shown with heat sealing areas H in FIG. 7C, heat sealing may be performed on places that cross the scheduled cut place C between the adjacent wearable articles 20 included in the continuous material W.

The thermal fusion pattern, i.e., an arrangement of the heat sealing areas H, is not limited to that shown in any of FIGS. 7A, 7B, and 7C. Any pattern may be formed with proviso that the superposed first part W1 and second part W2 of the continuous material W can be temporarily fastened together before the joining step to prevent occurrence of a discrepancy when the continuous material W is conveyed along the outer peripheral surface 5b of the rotary drum 5.

The movable part of the ultrasonic sealer unit 7 shown in FIGS. 2 to 3 may be any one of the anvil roller 10 and the ultrasonic horn 6.

Regarding the first part W1 corresponding to the front body and the second part W2 corresponding to the back body of the continuous material W, the continuous material is wound around the rotary drum 5 such that the first part W1 is disposed on an outer periphery side of the second part W2 in FIG. 5. However, they may be disposed in reverse, in other words, the continuous material may be wound around the rotary drum 5 such that the second part W2 is disposed on an outer periphery side of the first part W1.

The absorptive body A shown in FIG. 5 is folded in half (in other words, a first part A1 and a second part A2 are superposed on each other) since the first part W1 and the second part W2 of the continuous material W are superposed on each other in the superposing step (P4 in FIG. 1).

Characteristics of First Embodiment (1)

The method of the first embodiment for manufacturing the wearable article 20 as described above includes: a superposing step of superposing a first part W1 and a second part W2 of a wearable article 20 on each other, the wearable article 20 being included in a continuous material W, the first part W1 and the second part W2 corresponding to a front body and a back body respectively of the wearable article 20; a conveying step of winding the continuous material W including the first part W1 and the second part W2 superposed on each other around an outer peripheral surface 5b of a rotary drum 5, as shown in FIG. 5, and conveying the continuous material W by rotation of the rotary drum 5; and a joining step of moving a movable part (for example, an anvil roller 10) of each ultrasonic sealer unit 7 in FIGS. 2 to 3 outward and homeward in a cross direction R crossing a conveyance direction F in which the continuous material W is conveyed, with each of the ultrasonic sealer units 7 being rotated at a rate identical to a rate of the rotary drum 5 while the continuous material W is conveyed by the rotation of the rotary drum 5, to form linear sealing areas S1, S2 shown in FIG. 6 on an outward path R1 and a homeward path R2, respectively, and thereby joining the first part W1 and the second part W2 to each other through the formed linear sealing areas in areas corresponding to both sides of the wearable article 20, and the method further includes, after the superposing step and before the joining step, a discrepancy reduction step of inhibiting a movement of the first part W1 and the second part W2 relative to each other by temporary fastening such as heat sealing at a place at which the first part W1 and the second part W2 are to be joined together.

In the manufacturing method, in the discrepancy reduction step before the joining step of joining the first part W1 corresponding to the front body and the second part W2 corresponding to the back body of the wearable article 20 of the continuous material W to each other through the outward and homeward sealing areas, the movement of the first part W1 and the second part W2 relative to each other at a place at which the first part W1 and the second part W2 are to be joined together is inhibited by temporary fastening such as heat sealing. This, as shown in FIG. 6, makes it possible to form the sealing areas S1, S2 on the outward path R1 and the homeward path R2, respectively, along an identical place and reduce a discrepancy between the sealing areas S1, S2 at the time of joining the first part W1 and the second part W2 together. As a result, a peripheral velocity difference between the ultrasonic sealer unit 7 and either the first part W1 or the second part W2 can be reduced. This makes it possible to reduce a discrepancy between the sealing areas S1, S2 on the outward and homeward paths through which the superposed parts of the continuous material W are joined to each other.

Figure 11:
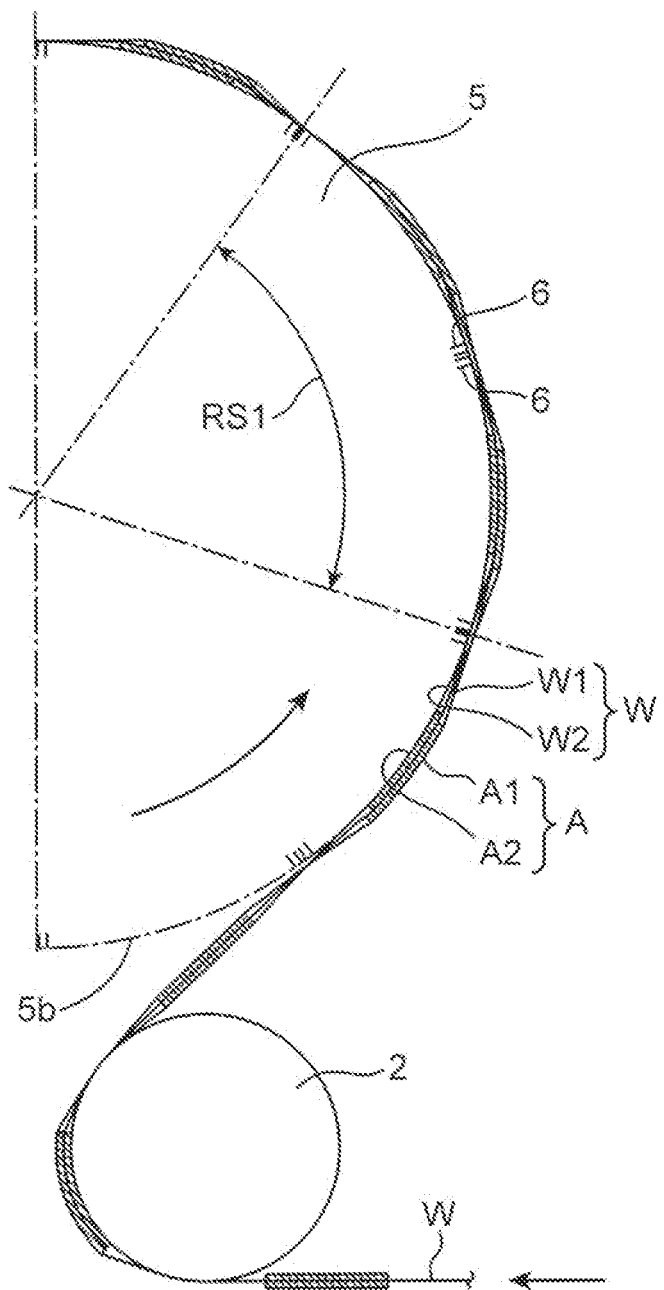
FIG. 11 is a drawing showing a situation in which a method for manufacturing a wearable article without a discrepancy reduction step in a comparative example of the present invention causes a difference in peripheral velocity between a first part and a second part superposed on each other of a continuous material on a rotary drum and the peripheral velocity difference results in a discrepancy between the first part and the second part.
Figure 12:
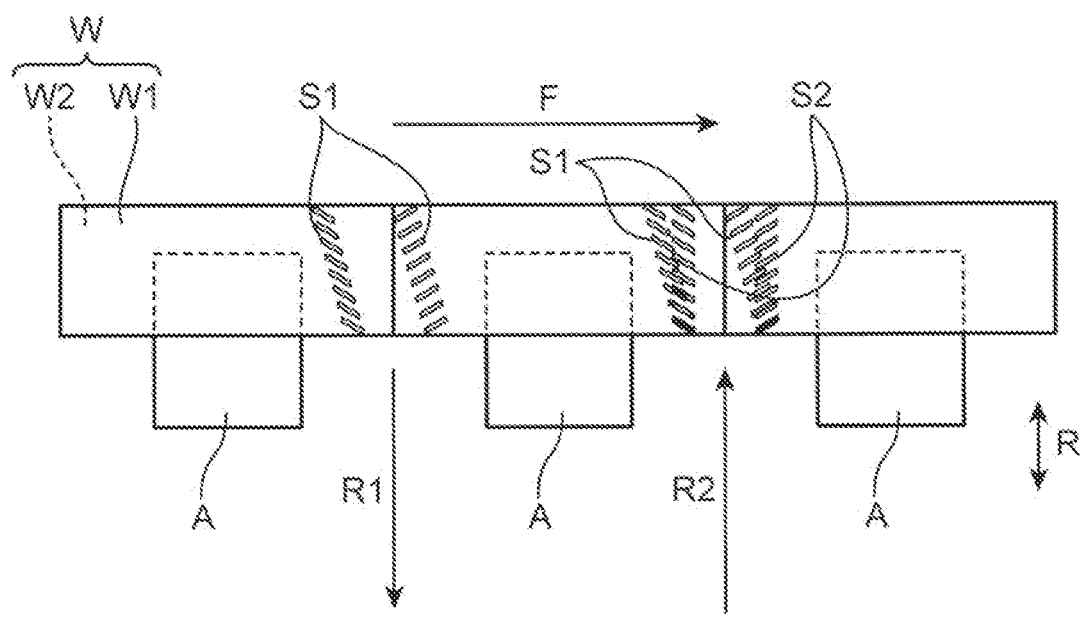
FIG. 12 is a drawing showing a discrepancy in sealing area between outward and homeward paths when outward and homeward sealing areas are formed over the rotary drum of FIG. 11.

In a comparative example where the discrepancy reduction step by temporary fastening such as heat sealing is not executed before the joining step, a peripheral velocity difference is made between the second part W2 disposed on the inner periphery side and the first part W1 disposed on the outer periphery side of the rotary drum 5 as shown in FIG. 11 when the continuous material W including the first part W1 and the second part W2 superposed on each other is wound around the rotary drum 5. This, as shown in FIG. 12, results in a problem of the occurrence of a discrepancy between the sealing areas S1, S2 on the outward path R1 and the homeward path R2 when the superposed parts are joined to each other by an outward-and-homeward movement of the ultrasonic sealer unit 7 in the cross direction R crossing the conveyance direction F for the continuous material W. Hence, it is clear that the discrepancy reduction step by temporary fastening such as heat sealing described above contributes to the effect of reducing a discrepancy between the outward and homeward sealing areas S1, S2 through which the superposed parts of the continuous material W are joined to each other.

(2)

In the discrepancy reduction step of the method of the first embodiment for manufacturing the wearable article 20, the first part W1 and the second part W2 are temporarily fastened to each other by heat sealing or other means at the scheduled joining place SO (see FIGS. 7A, 7B, and 7C) at which the first part W1 and the second part W2 are scheduled to be joined together or in an area adjacent to the scheduled joining place.

In the discrepancy reduction step of the manufacturing method, the first part W1 and the second part W2 are temporarily fastened to each other at the scheduled joining place SO for the first part W1 and the second part W2 or in an area adjacent to the scheduled joining place. This helps to reliably inhibit the movement of the first part W1 and the second part W2 relative to each other at the scheduled joining place SO before the joining step. This makes it possible to reliably reduce a discrepancy between the sealing areas S1, S2 on the outward path R1 and the homeward path R2 through which the first part W1 and the second part W2 are joined together.

Preferably, temporary fastening such as heat sealing is applied to as close as possible to the scheduled joining place SO to reduce a discrepancy between the outward and homeward sealing areas S1, S2 in the subsequent joining step.

Temporary fastening may be implemented at the outer peripheral surface 5b of the rotary drum 5, as well as at the peripheral surface of the bring-in anvil roller 2 on the upstream side in the conveyance direction F of the rotary drum 5.

(3)

In the method of the first embodiment for manufacturing the wearable article 20, in the joining step, the linear sealing areas S are formed at two places for two respective wearable articles adjacent to each other included in the continuous material W and are disposed between the two adjacent wearable articles, and in the discrepancy reduction step, the first part W1 and the second part W2 are temporarily fastened to each other between the two places (i.e., scheduled joining places) SO at which the linear sealing areas are scheduled to be formed.

With this configuration, in the discrepancy reduction step, as shown in FIGS. 7A, 7B, and 7C, the first part W1 and the second part W2 are temporarily fastened to each other between the two places (i.e., scheduled joining places) SO at which the linear sealing areas are scheduled to be formed. Thus, temporary fastening at a small number of places makes it possible to reduce a discrepancy between the sealing areas S1, S2 on the outward path R1 and the homeward path R2, which are the linear sealing areas S at the two places.

(4)

In the method of the first embodiment for manufacturing the wearable article 20, the temporary fastening is implemented by thermal fusion (heat sealing). This makes it possible to temporarily fasten the first part W1 and the second part W2 together by thermal fusion readily and quickly.

(5)
In the method of the first embodiment for manufacturing the wearable article 20, thermal fusion is performed along the scheduled cut place C between the adjacent wearable articles 20 included in the continuous material W. In this manufacturing method, thermal fusion is performed along the scheduled cut place C between the adjacent wearable articles 20 included in the continuous material W. Thus, when the adjacent wearable articles 20 are cut off each other along the cut place after the joining step, thermally fused areas (the heat sealing areas H in FIG. 7A(a)) are fragmented and inconspicuous.

(6)
In the method of the first embodiment for manufacturing the wearable article 20, thermal fusion may be performed on places on both sides of the scheduled cut place C between the adjacent wearable articles 20 included in the continuous material W. In this case, as shown with heat sealing areas H in FIG. 7B(b), thermal fusion is performed on places on both sides of the scheduled cut place C between the adjacent wearable articles 20 included in the continuous material W. As a result, many heat sealing areas H can be arranged. This makes it possible to reliably reduce a discrepancy between the sealing areas S1, S2 on the outward path R1 and the homeward path R2 through which the first part W1 and the second part W2 are joined together in areas corresponding to both sides of each wearable article 20 included in the continuous material W. When the adjacent wearable articles 20 are cut off each other along the cut place after the joining step, a cutter does not touch the heat sealing areas H. Thus, the heat sealing areas do not cause any resistance in cutting. Since the heat sealing areas H are not present on ends of the cut wearable article 20, there is no degradation in texture of the wearable article 20.

(7)
In the method of the first embodiment for manufacturing the wearable article 20, thermal fusion may be performed on places that cross the scheduled cut place C between the adjacent wearable articles 20 included in the continuous material W. In this case, as shown with heat sealing areas H in FIG. 7C(c), thermal fusion is performed on places that cross the scheduled cut place C between the adjacent wearable articles 20 included in the continuous material W. This allows both ends of thermally fused areas to come closer to the scheduled joining places, thus improving the effect of reducing a discrepancy between the sealing areas. In addition, when the adjacent wearable articles 20 are cut off each other along the cut place after the joining step, the thermally fused areas are fragmented and inconspicuous.

Modification Examples of First Embodiment (A)
In the first embodiment described above, thermal fusion (heat sealing) is taken as example means by which the first part W1 and the second part W2 of the continuous material W are temporarily fastened to each other in the discrepancy reduction step. However, the present invention is not limited to this example, and the temporary fastening may be implemented by another means. For instance, the temporary fastening may be implemented using a clip or other jigs or by embossing.

Figure 8:
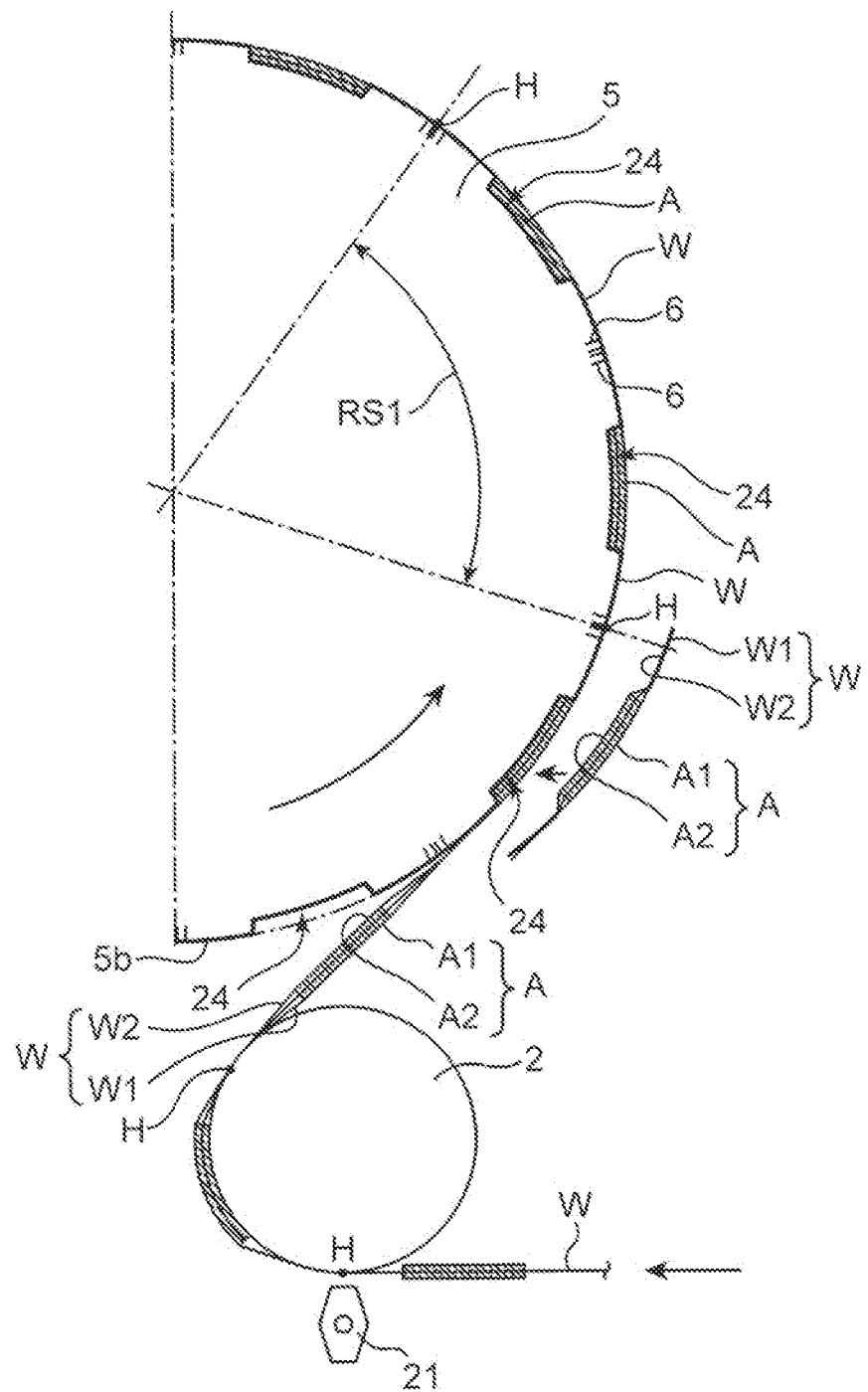
FIG. 8 is an illustrative drawing showing a process as another example of a discrepancy reduction step executed together with temporary fastening by heat sealing to enhance an effect of the temporary fastening by putting absorbers arranged at equal intervals on the continuous material into recesses formed in a peripheral surface of the rotary drum, according to a modification example of the first embodiment of the present invention.

(B)
In the method of the first embodiment for manufacturing the wearable article 20, in the discrepancy reduction step, the first part W1 and the second part W2 of the continuous material W are temporarily fastened to each other by heat sealing or other means. As shown in FIG. 8, to enhance the effect of temporary fastening, the absorptive body A of the wearable article 20 may be put into a recess 24 formed in the outer peripheral surface 5b of the rotary drum 5. The absorptive body A shown in FIG. 8 is folded in half (in other words, a first part A1 and a second part A2 are superposed on each other) since the first part W1 and the second part W2 of the continuous material W are superposed on each other in the superposing step (P4 in FIG. 1).

Specifically, a method of a modification example of the first embodiment for manufacturing the wearable article 20, wherein
  (a) in the superposing step, the first part W1 and the second part W2 of the continuous material W are superposed on each other, with an absorptive body A being interposed between the first part W1 and the second part W2,
  (b) in the conveying step, as shown in FIG. 8, with at least a part (in FIG. 8, a whole) of the absorptive body A being put into a recess 24 formed in the outer peripheral surface 5b of the rotary drum 5, the continuous material W including the first part W1 and the second part W2 superposed on each other is wound around the outer peripheral surface 5b of the rotary drum 5 and is conveyed by rotation of the rotary drum 5, and
  (c) in the joining step, with the first part W1 and the second part W2 being temporarily fastened to each other through the heat sealing areas H or the like and the at least part of the absorptive body A being put into the recess 24 while the rotary drum 5 in FIG. 8 is rotated in a predetermined angular range RS1, for example, the first part W1 and the second part W2 are joined together by the ultrasonic sealer unit 7 (see FIGS. 2 to 3) including the ultrasonic horn 6 disposed on the outer peripheral surface 5b of the rotary drum 5.

In the manufacturing method of the modification example shown in FIG. 8, in the joining step, at the time of joining the first part W1 and the second part W2 together, the first part W1 and the second part W2 of the continuous material W are temporarily fastened to each other through the heat sealing areas H or the like, and moreover, the at least part of the absorptive body A is put into the recess 24 to enhance the effect of temporary fastening. This makes it possible to reliably reduce a discrepancy between the sealing areas S1, S2 on the outward path R1 and the homeward path R2 through which the first part W1 and the second part W2 of each wearable article 20 included in the continuous material W are joined together.

The at least part of the absorptive body A is put into the recess 24 and thus a difference in path length between the first part W1 and the second part W2 of the continuous material W on a peripheral surface of the rotary drum 5 decreases. This also improves the effect of reducing a discrepancy between the sealing areas S1, S2 on the outward path R1 and the homeward path R2.

Second Embodiment

In the method of the first embodiment for manufacturing the wearable article 20, the discrepancy reduction step by temporary fastening such as heat sealing is executed before the joining step. As a discrepancy reduction step without temporary fastening such as heat sealing, a discrepancy reduction step may be executed using a needle-shaped member disposed on the outer peripheral surface 5b of the rotary drum 5.

Figure 9:
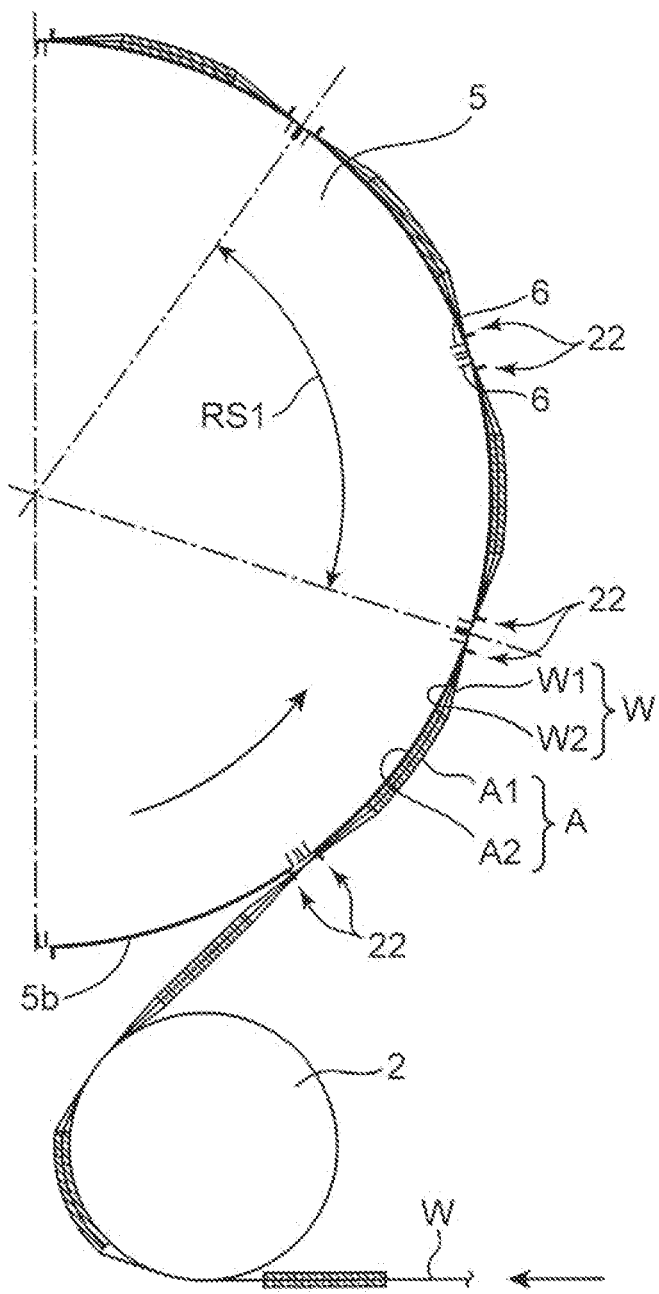
FIG. 9 is an illustrative drawing showing a process, in a method for manufacturing a wearable article according to a second embodiment of the present invention, executed to reduce a discrepancy between a first part and a second part superposed on each other of a continuous material by causing a plurality of needles disposed on a peripheral surface of a rotary drum to penetrate through the first part and the second part in a discrepancy reduction step.

Specifically, in a method of a second embodiment for manufacturing the wearable article 20, in the discrepancy reduction step, as shown in FIGS. 9 to 10, in an area adjacent to a place (the scheduled joining places S0) at which the first part W1 and the second part W2 of the continuous material W are to be joined together, the first part W1 and the second part W2 are penetrated by a needle-shaped member, i.e., a large number of needles 22, disposed on the rotary drum 5 to inhibit a movement of the first part W1 and the second part W2 relative to each other. The superposing step, the conveying step, and the joining step in the manufacturing method are shared with the first embodiment described above, and thus a description of these steps is omitted.

Figure 10B:
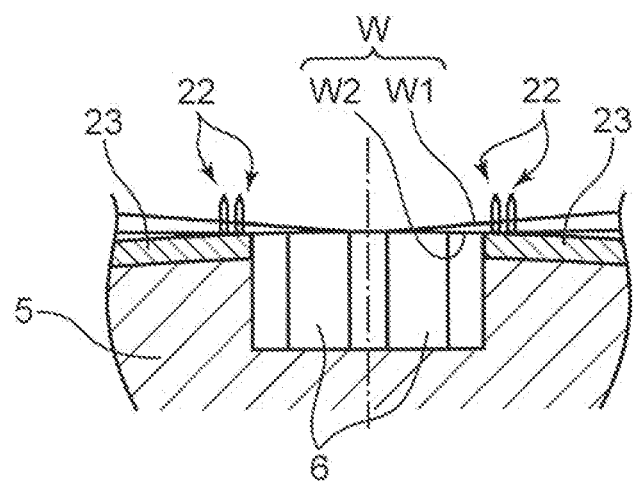
FIG. 10B is an illustrative cross-sectional view showing a situation in which the first part and the second part of the continuous material are penetrated by the needles of FIG. 10A on the peripheral surface of the rotary drum.
Figure 10C:
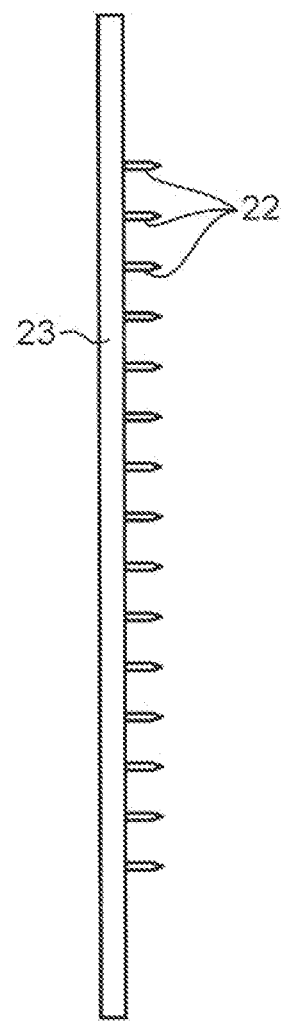
FIG. 10C is a side view of a plate supporting the needles of FIG. 10A.

The large number of the needles 22 supported by a plate 23, shown in FIGS. 10A, 10B, and 10C, are disposed on the outer peripheral surface 5b of the rotary drum 5. The large number of the needles 22 are arranged on opposing sides of the scheduled cut place C along the scheduled joining places S0 and confront each other through the scheduled joining places S0.

Any needle-shaped member other than the large number of the needles 22 may be used with proviso that the needle-shaped member can penetrate through the first part W1 and the second part W2.

A length of each needle 22 may be a length such that the needle can penetrate through the first part W1 and the second part W2 of the continuous material W and that the continuous material W does not get caught on the needle 22 when being detached from the rotary drum 5. Preferably, the needle 22 is thin and short in that the needle does not damage the continuous material W when penetrating through the continuous material W.

In the method of the second embodiment for manufacturing the wearable article 20, shown in FIGS. 10A, 10B, 10C, and 11, in the discrepancy reduction step, the first part W1 and the second part W2 are penetrated by the needle-shaped member (in FIGS. 10A, 10B, 10C, and 11, the large number of the needles 22) disposed on the rotary drum 5 to inhibit the movement of the first part W1 and the second part W2 relative to each other. This helps to reliably inhibit the movement of the first part W1 and the second part W2 relative to each other at the scheduled joining places before the joining step (for example, ultrasonic welding during rotation of the rotary drum 5 in the predetermined angular range RST in FIG. 9). This makes it possible to reliably reduce a discrepancy between the sealing areas S1, S2 on the outward path R1 and the homeward path R2 through which the first part W1 and the second part W2 are joined together. Moreover, even if the continuous material W is made of a material resistant to thermal fusion, the movement of the first part W1 and the second part W2 relative to each other can be inhibited by the needle-shaped member. This increases versatility of the present manufacturing method.

OTHER EMBODIMENTS

In the first and the second embodiments, the methods for manufacturing the wearable article such as a disposable diaper that includes a front body and a back body have been described to give an example. However, the present invention should not be limited to this example. The manufacturing method of the present invention can be applied to a pouch-shaped wearable article such as a sanitary pad that is manufactured by superposing a first part and a second part of a continuous material on each other with an absorptive body put between the first part and the second part and thereby joining the first part and the second part together.

SUMMARY OF EMBODIMENTS

The embodiments are summarized as follows.

A method for manufacturing a wearable article, according to the embodiments described above, includes: a superposing step of superposing a first part and a second part of a wearable article on each other, the wearable article being included in a continuous material; a conveying step of winding the continuous material including the first part and the second part superposed on each other around an outer peripheral surface of a rotary drum and conveying the continuous material by rotation of the rotary drum; and a joining step of moving a movable part of a sealer unit outward and homeward in a cross direction crossing a conveyance direction in which the continuous material is conveyed, with the sealer unit being rotated at a rate identical to a rate of the rotary drum while the continuous material is conveyed by the rotation of the rotary drum, to form linear sealing areas on an outward path and a homeward path, respectively, and thereby joining the first part and the second part to each other through the formed linear sealing areas in areas corresponding to both sides of the wearable article, and the method further includes, after the superposing step and before the joining step, a discrepancy reduction step of inhibiting a movement of the first part and the second part relative to each other at a place at which the first part and the second part are to be joined together.

In the manufacturing method, in the discrepancy reduction step before the joining step of joining the first part corresponding to the front body and the second part corresponding to the back body of the wearable article of the continuous material to each other through the outward and homeward sealing areas, the movement of the first part and the second part relative to each other is inhibited at a place at which the first part and the second part are to be joined together. This makes it possible to reduce a discrepancy between the sealing areas on the outward path and the homeward path at the time of joining the first part and the second part together. As a result, a peripheral velocity difference between the sealer unit and either the first part or the second part can be reduced. This makes it possible to reduce a discrepancy between the sealing areas on the outward and homeward paths through which the superposed parts of the continuous material are joined to each other.

Preferably, in the method for manufacturing the wearable article, in the discrepancy reduction step, the first part and the second part are temporarily fastened to each other at a scheduled joining place at which the first part and the second part are scheduled to be joined together or in an area adjacent to the scheduled joining place.

In the manufacturing method, in the discrepancy reduction step, the first part and the second part are temporarily fastened to each other at the scheduled joining place for the first part and the second part or in an area adjacent to the scheduled joining place. This helps to reliably inhibit the movement of the first part and the second part relative to each other at the scheduled joining place before the joining step. This makes it possible to reliably reduce a discrepancy between the sealing areas on the outward path and the homeward path through which the first part and the second part are joined together.

Preferably, in the method for manufacturing the wearable article, in the joining step, the linear sealing areas are formed at two places for two of the respective wearable articles adjacent to each other included in the continuous material and are disposed between the two adjacent wearable articles, and preferably, in the discrepancy reduction step, the first part and the second part are temporarily fastened to each other between the two places at which the linear sealing areas are scheduled to be formed.

With this configuration, in the discrepancy reduction step, the first part and the second part are temporarily fastened to each other between the two places at which the linear sealing areas are scheduled to be formed. Thus, temporary fastening at a small number of places makes it possible to reduce a discrepancy between the sealing areas on the outward path and the homeward path, which are the linear sealing areas at the two places.

Preferably, in the method for manufacturing the wearable article, the temporary fastening is implemented by thermal fusion.

In the manufacturing method, it is possible to temporarily fasten the first part and the second part together by thermal fusion readily and quickly.

Preferably, in the method for manufacturing the wearable article, the thermal fusion is performed along a scheduled cut place between the adjacent wearable articles included in the continuous material.

In the manufacturing method, thermal fusion is performed along the scheduled cut place between the adjacent wearable articles included in the continuous material. Thus, when the adjacent wearable articles are cut off each other along the cut place after the joining step, thermally fused areas are fragmented and inconspicuous.

In the method for manufacturing the wearable article, the thermal fusion may be performed on places on both sides of a scheduled cut place between the adjacent wearable articles included in the continuous material.

In the manufacturing method, thermal fusion is performed on places on both sides of the scheduled cut place between the adjacent wearable articles included in the continuous material. As a result, many thermally fused places can be arranged. This makes it possible to reliably reduce a discrepancy between the sealing areas on the outward path and the homeward path through which the first part and the second part are joined together in areas corresponding to both sides of each wearable article included in the continuous material. When the adjacent wearable articles are cut off each other along the cut place after the joining step, a cutter does not touch the thermally fused areas. Thus, the thermally fused areas do not cause any resistance in cutting.

In the method for manufacturing the wearable article, the thermal fusion may be performed on places that cross a scheduled cut place between the adjacent wearable articles included in the continuous material.

In the manufacturing method, thermal fusion is performed on places that cross the scheduled cut place between the adjacent wearable articles included in the continuous material. This allows both ends of thermally fused areas to come closer to the scheduled joining places, thus improving the effect of reducing a discrepancy between the sealing areas. In addition, when the adjacent wearable articles are cut off each other along the cut place after the joining step, the thermally fused areas are fragmented and inconspicuous.

Preferably, in the method for manufacturing the wearable article, in the superposing step, the first part and the second part are superposed on each other, with an absorptive body being interposed between the first part and the second part, in the conveying step, with at least a part of the absorptive body being put into a recess formed in the outer peripheral surface of the rotary drum, the continuous material including the first part and the second part superposed on each other is wound around the outer peripheral surface of the rotary drum and is conveyed by rotation of the rotary drum, and in the joining step, with the first part and the second part being temporarily fastened to each other and the at least part of the absorptive body being put into the recess, the first part and the second part are joined together.

In the manufacturing method, in the joining step, at the time of joining the first part and the second part together, the first part and the second part of the continuous material are temporarily fastened to each other, and moreover, the at least part of the absorptive body is put into the recess to enhance the effect of temporary fastening. This makes it possible to reliably reduce a discrepancy between the sealing areas on the outward path and the homeward path through which the first part and the second part of each wearable article included in the continuous material are joined together.

In the method for manufacturing the wearable article, in the discrepancy reduction step, in an area adjacent to a place at which the first part and the second part of the continuous material are to be joined together, the first part and the second part may be penetrated by a needle-shaped member disposed on the rotary drum to inhibit a movement of the first part and the second part relative to each other.

In the manufacturing method, in the discrepancy reduction step, the first part and the second part are penetrated by the needle-shaped member disposed on the rotary drum to inhibit the movement of the first part and the second part relative to each other. This helps to reliably inhibit the movement of the first part and the second part relative to each other at the scheduled joining places before the joining step. This makes it possible to reliably reduce a discrepancy between the sealing areas on the outward path and the homeward path through which the first part and the second part are joined together. Moreover, even if the continuous material is made of a material resistant to thermal fusion, the movement of the first part and the second part relative to each other can be inhibited by the needle-shaped member. This increases versatility of the present manufacturing method.

The method for manufacturing the wearable article described in the above embodiments has a capability to reduce a discrepancy between sealing areas on outward and homeward paths through which superposed parts of a continuous material are joined to each other.

The invention claimed is:

1. A method for manufacturing a wearable article, the method comprising:
   a superposing step of superposing a first part of the wearable article and a second part of the wearable article on each other, the wearable article being included in a continuous material;
   a conveying step of winding the continuous material including the first part and the second part superposed on each other around an outer peripheral surface of a rotary drum and conveying the continuous material by rotation of the rotary drum;
   a joining step of moving a movable part of a sealer unit outward and homeward in a cross direction crossing a conveyance direction in which the continuous material is conveyed, with the sealer unit being rotated at a rate identical to a rate of the rotary drum while the continuous material is conveyed by the rotation of the rotary drum, to form linear sealing areas on an outward path and a homeward path, respectively, and thereby joining the first part and the second part to each other through the linear sealing areas in areas corresponding to both sides of the wearable article, wherein the linear sealing areas are formed on the wearable article and on another wearable article adjacent to the wearable article;
a cutting step of cutting the continuous material between one of the linear sealing areas of the wearable article and one of the linear sealing areas of the other wearable article adjacent to the wearable article; and
after the superposing step and before the joining step and the cutting step, a discrepancy reduction step of inhibiting a movement of the first part and the second part relative to each other at a place at which the first part and the second part are to be joined together.

2. The method according to claim 1, wherein, in the discrepancy reduction step, the first part and the second part are temporarily fastened to each other at a scheduled joining place at which the first part and the second part are scheduled to be joined together or in an area adjacent to the scheduled joining place.

3. The method according to claim 2, wherein, in the discrepancy reduction step, the first part and the second part are temporarily fastened to each other between two places at which the one of the linear sealing areas of the wearable article and the one of the linear sealing areas of the other wearable article are scheduled to be formed.

4. The method according to claim 2, wherein the temporary fastening is implemented by thermal fusion.

5. The method according to claim 4, wherein the thermal fusion is performed along a scheduled cut place between the wearable article and the other wearable article adjacent to the wearable article.

6. The method according to claim 4, wherein the thermal fusion is performed on places on both sides of a scheduled cut place between the wearable article and the other wearable article adjacent to the wearable article.

7. The method according to claim 4, wherein the thermal fusion is performed on places that cross a scheduled cut place between the wearable article and the other wearable article adjacent to the wearable article.

8. The method according to claim 2, wherein:
in the superposing step, the first part and the second part are superposed on each other, with an absorptive body being interposed between the first part and the second part;
in the conveying step, with at least part of the absorptive body being put into a recess formed in the outer peripheral surface of the rotary drum, the continuous material including the first part and the second part superposed on each other is wound around the outer peripheral surface of the rotary drum and is conveyed by the rotation of the rotary drum; and
in the joining step, with the first part and the second part being temporarily fastened to each other and the at least part of the absorptive body being put into the recess, the first part and the second part are joined together.

9. The method according to claim 1, wherein, in the discrepancy reduction step, in an area adjacent to the place at which the first part and the second part are to be joined together, the first part and the second part are penetrated by a needle-shaped member disposed on the rotary drum to inhibit the movement of the first part and the second part relative to each other.

10. The method according to claim 3, wherein the temporary fastening is implemented by thermal fusion.

11. The method according to claim 10, wherein the thermal fusion is performed along a scheduled cut place between the wearable article and the other wearable article adjacent to the wearable article.

12. The method according to claim 10, wherein the thermal fusion is performed on places on both sides of a scheduled cut place between the wearable article and the other wearable article adjacent to the wearable article.

13. The method according to claim 10, wherein the thermal fusion is performed on places that cross a scheduled cut place between the wearable article and the other wearable article adjacent to the wearable article.

14. The method according to claim 3, wherein:
in the superposing step, the first part and the second part are superposed on each other, with an absorptive body being interposed between the first part and the second part;
in the conveying step, with at least part of the absorptive body being put into a recess formed in the outer peripheral surface of the rotary drum, the continuous material including the first part and the second part superposed on each other is wound around the outer peripheral surface of the rotary drum and is conveyed by the rotation of the rotary drum; and
in the joining step, with the first part and the second part being temporarily fastened to each other and the at least part of the absorptive body being put into the recess, the first part and the second part are joined together.

15. The method according to claim 4, wherein:
in the superposing step, the first part and the second part are superposed on each other, with an absorptive body being interposed between the first part and the second part;
in the conveying step, with at least part of the absorptive body being put into a recess formed in the outer peripheral surface of the rotary drum, the continuous material including the first part and the second part superposed on each other is wound around the outer peripheral surface of the rotary drum and is conveyed by the rotation of the rotary drum; and
in the joining step, with the first part and the second part being temporarily fastened to each other and the at least part of the absorptive body being put into the recess, the first part and the second part are joined together.

16. The method according to claim 5, wherein:
in the superposing step, the first part and the second part are superposed on each other, with an absorptive body being interposed between the first part and the second part;
in the conveying step, with at least part of the absorptive body being put into a recess formed in the outer peripheral surface of the rotary drum, the continuous material including the first part and the second part superposed on each other is wound around the outer peripheral surface of the rotary drum and is conveyed by the rotation of the rotary drum; and
in the joining step, with the first part and the second part being temporarily fastened to each other and the at least part of the absorptive body being put into the recess, the first part and the second part are joined together.

17. The method according to claim 6, wherein:
in the superposing step, the first part and the second part are superposed on each other, with an absorptive body being interposed between the first part and the second part;
in the conveying step, with at least part of the absorptive body being put into a recess formed in the outer peripheral surface of the rotary drum, the continuous material including the first part and the second part superposed on each other is wound around the outer peripheral surface of the rotary drum and is conveyed by the rotation of the rotary drum; and in the joining step, with the first part and the second part being temporarily fastened to each other and the at least part of the absorptive body being put into the recess, the first part and the second part are joined together.

18. The method according to claim 7, wherein:

in the superposing step, the first part and the second part are superposed on each other, with an absorptive body being interposed between the first part and the second part;

in the conveying step, with at least part of the absorptive body being put into a recess formed in the outer peripheral surface of the rotary drum, the continuous material including the first part and the second part superposed on each other is wound around the outer peripheral surface of the rotary drum and is conveyed by the rotation of the rotary drum; and in the joining step, with the first part and the second part being temporarily fastened to each other and the at least part of the absorptive body being put into the recess, the first part and the second part are joined together.

19. The method according to claim 11, wherein:

in the superposing step, the first part and the second part are superposed on each other, with an absorptive body being interposed between the first part and the second part;

in the conveying step, with at least part of the absorptive body being put into a recess formed in the outer peripheral surface of the rotary drum, the continuous material including the first part and the second part superposed on each other is wound around the outer peripheral surface of the rotary drum and is conveyed by the rotation of the rotary drum; and in the joining step, with the first part and the second part being temporarily fastened to each other and the at least part of the absorptive body being put into the recess, the first part and the second part are joined together.

20. The method according to claim 12, wherein:

in the superposing step, the first part and the second part are superposed on each other, with an absorptive body being interposed between the first part and the second part;

in the conveying step, with at least part of the absorptive body being put into a recess formed in the outer peripheral surface of the rotary drum, the continuous material including the first part and the second part superposed on each other is wound around the outer peripheral surface of the rotary drum and is conveyed by the rotation of the rotary drum; and in the joining step, with the first part and the second part being temporarily fastened to each other and the at least part of the absorptive body being put into the recess, the first part and the second part are joined together.

21. The method according to claim 1, wherein:

in the cutting step, the continuous material is cut in a scheduled cut place between the one of the linear sealing areas of the wearable article and the one of the linear sealing areas of the other wearable article;

the one of the linear sealing areas of the wearable article and the one of the linear sealing areas of the other wearable article are defined in two places separated from each other across a cutting zone that is defined for cutting off the wearable article and the other wearable article adjacent to the wearable article; and in the discrepancy reduction step, the first part and the second part are temporarily fastened to each other by thermal fusion in the scheduled cut place.

* * * * *